United States Patent [19]

Hoda et al.

[11] 4,454,237

[45] Jun. 12, 1984

[54] ORGANIC-INORGANIC COMPOSITES CONTAINING SYNTHETIC MICA

[75] Inventors: Syed N. Hoda, Horseheads; Anthony R. Olszewski, Bath, both of N.Y.

[73] Assignee: Corning Glass Works, Corning, N.Y.

[21] Appl. No.: 461,571

[22] Filed: Jan. 27, 1983

[51] Int. Cl.$^3$ ............................ C03C 3/22; C09C 1/02
[52] U.S. Cl. ........................................... 501/2; 65/33; 106/291; 106/306; 106/308 N; 106/308 Q; 106/DIG. 3; 264/325; 428/363; 501/3; 501/4; 501/12; 501/36; 501/151
[58] Field of Search ............ 106/DIG. 3, 291, 308 M, 106/308 Q, 308 N, 306; 501/3, 12, 151, 36, 2, 4; 264/325

[56] References Cited

U.S. PATENT DOCUMENTS 4,239,519 12/1980 Beall ........................................ 501/3
4,341,824 7/1982 Le Grand ........................ 106/308 M

*Primary Examiner*—Helen M. McCarthy
*Attorney, Agent, or Firm*—C. S. Janes, Jr.

[57] ABSTRACT

This invention is directed to the preparation of an organic-inorganic composite body demonstrating hydrophobic behavior containing crystals of an organic polycation-exchanged lithium and/or sodium water-swelling mica, the organic polycation being selected from the group of aminosilanes and organic chrome complexes. The process of preparing such products contemplates the steps of:

(a) forming a glass-ceramic body containing crystals selected from the group of fluorhectorite, hydroxyl hectorite, boron fluorphlogopite, hydroxyl boron phlogopite, and solid solutions among those and between those and other structurally-compatible species selected from the group of talc, fluortalc, polylithionite, fluorpolylithionite, phlogopite, and fluorphlogopite;

(b) contacting said body with a polar liquid for a time sufficient to cause swelling and disintegration thereof accompanied with the formation of a gel; and (c) contacting said gel with a source of organic polycations selected from the group of aminosilanes and chrome complexes to cause an ion exchange reaction to occur between said polycations and the Li$^+$ and/or Na$^+$ ions from the interlayer of said crystals, whereby essentially all of said Li$^+$ and/or Na$^+$ ions are replaced with said organic polycations.

Paper, board, film, fiber, and coating can be formed from the exchanged gel, and dried powders thereof can be hot pressed to yield a body consisting of a crosslinked organic polycation-mica derivative.

8 Claims, No Drawings

ORGANIC-INORGANIC COMPOSITES CONTAINING SYNTHETIC MICA

BACKGROUND OF THE INVENTION

U.S. Pat. No. 4,239,519 describes the preparation of inorganic, crystal-containing gels and papers, fibers, films, boards, and coatings produced from those gels. The process for preparing the gels comprised three basic elements:

(a) a fully or predominantly crystalline body is formed (a glass-ceramic is the preferred embodiment) which contains crystals consisting essentially of a lithium and/or sodium water-swelling mica selected from the group of fluorhectorite, hydroxyl hectorite, boron fluorphlogopite, hydroxyl boron phlogopite, and solid solutions between those and other structurally-compatible species selected from the grop of talc, fluortalc, polylithionite, fluorpolylithionite, phlogopite, and fluorphlogopite;

(b) that body is contacted with a polar liquid, conveniently water, to cause swelling and disintegration of the body accompanied with the formation of a gel; and (c) the solid:liquid ratio of the gel is adjusted to a desired level depending upon the application therefor.

Particularly useful base compositions are stated to consist essentially, expressed in terms of weight percent on the oxide basis, of $Li_2O$: 0–12
$Na_2O$: 0–10
$Li_2O+Na_2O$: 0.5–14
$MgO$: 10–38
$B_2O_3$: 0–30
$Al_2O_3$: 0–10
$SiO_2$: 35–70
F: 0–15
OH: 0–15
F+OH: 4–15

To confer good chemical durability to papers, films, fibers, boards, and coatings produced from the gels, those products are contacted with a source of large cations to cause flocculation of the gel and an ion exchange reaction to occur between the large cations and the $Li^+$ and/or $Na^+$ ions from the interlayer of the crystals. Normally, the ion exchanged products will be subsequently washed and dried. The patent discloses $K^+$, $Rb^+$, $Cs^+$, $NH_4^+$, $H_3O^+$, $Ca^{+2}$, $Sr^{+2}$, $Ba^{+2}$, $Pb^{+2}$, $Cu^+$, $Ag^+$, and certain organic polycations, specifically naming aniline hydrochloride and quaternary ammonium compounds, as illustrative of large cations operable in the ion exchange reaction. If desired, the ion exchange may be carried out with the gel, i.e., before a paper, film, fiber, board, coating, or other product is fashioned, or during the process for actually forming the product. In any event, no matter where the ion exchange is conducted in the stream of production, its occurrence is demanded to avoid spontaneous disintegration of the products in the presence of water.

Long term testing of articles formed in accordance with the description of that patent has demonstrated that the values of such physical properties as mechanical strength, flexibility, dielectric strength, loss tangent, and ionic conductivity are modified by the relative humidity of the ambient environment. In other words, the properties exhibited by the products do not manifest long term stability when exposed to humid atmospheres. Thus, there is normally an overall deterioration in the electrical and mechanical properties as the relative humidity of the surrounding environment is increased.

The use of finely-divided mica as an inexpensive filler in organic plastics has long been practiced. Hence, the mica not only reduces the cost of the products but also stiffens the plastic so that mold shrinkage is considerably reduced. However, the loading of mica into the plastic is commonly held below about 30% by weight since the mechanical strength of the product is adversely affected at higher loadings. Very recently (Rosalind, J., "Non-Fibrous Reinforcements", *Modern Plastics*, July, 1982, pages 46–48) it has been shown that, by utilizing certain forming conditions and practices, the flexural strength and Young's modulus of the plastic product can be increased as much as threefold through loadings of mica of 40–50% by weight. The absolute strength of the final article will still customarily be less than that imparted through glass fiber reinforcement but the mica provides other advantages. Thus, the mica flakes tend to assume parallel orientation during the flow of the plastic, thereby resulting in a "fish-scale" structure which resists point impacts, infiltration, and corrosion. Moreover, the mica flakes can be packed much more solidly than glass fibers which permits advantage to be taken of high volume content in this composites.

As is explained in U.S. Pat. No. 4,239,519, the crystals developed exhibit a morphology of a continuum of flakes, rectangular-like strips, and interwoven ribbons in parallel or sub-parallel zones or sheaths with said flakes being irregularly shaped with diameters between about 0.5–10 microns and cross sections of less than 100 Å, and said strips and ribbons being about 0.5–10 microns long, about 500–5000 Å wide, and less than about 100 Å thick. Such morphology results in the crystals demonstrating a very high aspect ratio, higher than naturally-occurring mica, and large surface area, both of those features serving to recommend the utility of the materials for reinforcing plastic bodies.

SUMMARY OF THE INVENTION

As was observed above, U.S. Pat. No. 4,239,519 discloses that the $Li^+$ and/or $Na^+$ ions in the crystals can be replaced in an aqueous gel with essentially any cation or cationic group. The academic literature (Grim, R. E., *Clay Mineralogy*, McGraw-Hill Book Company, Inc., New York, 1953, pages 251–277) notes that alkyl ammonium and its derivatives can replace interlayer cations in naturally-occurring montmorillonite and related minerals. However, the goal of the present invention was to modify the surface of the crystals produced in accordance with U.S. Pat. No. 4,239,519 with an organic species that could either be polymerized by itself to form a coherent mass or would be reactive with the crystals at one end and a suitable resin on the other end, thereby chemically tying the two together. It was recognized that, when functioning as a coupling agent, the presence of the organic species in the interlayer sites of the crystals would not be necessary and would simply add to the cost of the final product. On the other hand, it was speculated that a self-polymerizing organic derivative of the crystals might demand replacement of $Li^+$ and/or $Na^+$ ions by a cationic monomer or a partially polymerized species.

With those factors in mind, the following organic species were investigated: urea, thiourea, conventional silane coupling agents, hexamethyl disilazane, organic chrome complexes, and aminosilanes. Only the latter two groups evidenced very strong bonding with the crystals. Furthermore, contact with those two agents imparts hydrophobic behavior to papers, films, fibers, boards, and coatings prepared in according with U.S. Pat. No. 4,239,519.

In general, only an amount of aminosilane and/or organic chrome complex sufficient to replace essentially all of the $Li^+$ and/or $Na^+$ ions in the interlayer of the mica crystals will be utilized. The composites may be dried and cured by heating to slightly elevated temperatures, i.e., temperatures above room temperature but normally not in excess of 200° C.

RELATED PATENT APPLICATION

U.S. application Ser. No. 461,672, filed concurrently herewith by Shy-Hsien Wu and entitled ORGANIC-INORGANIC COMPOSITES OF NEUTRALIZED POLYELECTROLYTE COMPLEXES, discloses the production of neutralized polyelectrolyte complexes exhibiting hydrophobic behavior by contacting a gel prepared in accordance with U.S. Pat. No. 4,239,519 with a source of organic polycations for a sufficient length of time to effect an ion exchange reaction between the organic polycations and interlayer $Li^+$ and/or $Na^+$ ions of the crystals, and to neutralize the charge density of the crystals. Particularly useful organic polycations are selected from the group of:

(1) a primary amine solubilized with acid;
(2) a secondary amine solubilized with acid;
(3) a tertiary amine solubilized with acid;
(4) a quaternary ammonium acid salt;
(5) a quaternary phosphonium acid salt; and
(6) a ternary sulfonium acid salt.

DESCRIPTION OF PREFERRED EMBODIMENTS

Illustrative of an operable aminosilane is Z6020, the designation applied by Dow Corning Corporation, Midland, Michigan to the compound N-β-aminoethyl-γ-aminopropyl trimethoxy silane. The compound contains primary and secondary amine groups which can combined with such different resins as epoxy, melamine, and phenolic. It polymerizes in water by a condensation reaction of the trimethoxy group. Heat, strong bases, and acids accelerate the polymerization.

In order to retard the rate of polymerization and thereby avert the formation of an insoluble mass, dilute aqueous solutions of 10-25% by weight were utilized. The pH of the solutions was reduced from about 10 to 6.5-7 through the addition of acetic acid. In like manner, the pH of the gel was lowered from 11-11.5 to 6.5-7. The aminosilane solution was admixed into the gel with stirring at room temperature. Flocculation of the gel occurred in similar fashion to that observed through the addition of a potassium salt solution, the preferred mode of flocculation disclosed in U.S. Pat. No. 4,239,519. The floc was strongly coherent and formed a tough body when dried. Where the pH is not preadjusted to approach neutrality, flocculation will occur, but the floc is not coherent and a weak body is formed when the mass is dried.

Table I reports chemically analytical data relating to the room temperature flocculation, by a 6.3% by weight aqueous solution of Z6020 and by a 7% by weight aqueous solution of KCl, of an aqueous gel prepared in accordance with the procedure disclosed in U.S. Pat. No. 4,239,519 from the following composition, expressed in terms of weight percent on the oxide basis:

$SiO_2$: 59.8
MgO: 23.7
$Li_2O$: 6.2
F: 10.3

The pH of the gel to be flocculated with Z6020 was decreased to 6.5 prior to mixing through the addition of acetic acid. Both flocs were washed several times with distilled water to remove excess Z6020 and KCl and then dried in an oven at 110° C.

TABLE I

| | Base Composition | Z6020 Floc | Z6020 Floc Normalized | KCl Floc |
|---|---|---|---|---|
| $SiO_2$ | 59.8 | 55.2 | 59.9 | 57.8 |
| MgO | 23.7 | 18.9 | 20.5 | 23.5 |
| $Li_2O$ | 6.2 | 2.6 | 2.8 | 2.6 |
| F | 10.3 | 7.3 | 7.9 | 8.8 |
| C | — | 5.7 | 6.2 | — |
| N | — | 2.4 | 2.6 | — |
| $K_2O$ | — | — | — | 7.1 |
| *$LOD_{110°}$ C. | — | 5.1 | — | — |
| **$LOI_{500°}$ C. | — | 9.3 | — | — |
| **$LOI_{900°}$ C. | — | 5.1 | — | — |

*Loss on drying
**Loss on ignition

The carbon:nitrogen ratio (C:N) in the Z6020 floc of 2.385 was somewhat higher than would be expected inasmuch as the carbon content of Z6020 is about 31.7% and that of nitrogen about 14.8%, yielding a C:N ratio of about 2.14. This apparent anomaly may have resulted from sorbed acetic acid which tends to carbonize on the floc mass upon heating. Utilizing the nitrogen content to estimate the quantity of Z6020 bonded to the floc, it appears that the Z6020 exchange floc contained about 16.5% by weight of the aminosilane. It can be observed that the level of residual $Li_2O$ in the floc is approximately the same in the Z6020 exchanged and the KCl exchanged samples.

Because of the rapidity of the exchange reaction and the cohesion of the resultant floc, it is possible to continuously draw a film utilizing the above gel composition and a bath of a 20% by weight aqueous solution of Z6020 in like manner to that described in U.S. Pat. No. 4,239,519.

To investigate the possibility of forming a body of Z6020 exchanged mass cross-linked at elevated temperature and pressure, the following procedure was undertaken. The exchange was conducted in the manner described above but the floc was washed repeatedly with acetone before drying in order to avoid hardening. The resultant residue was then reduced to powder. When the powder was hot pressed for one hour at 300° C. under a pressure of 10,000 psi, cross-linking of the aminosilane mica derivative occurred yielding a light weight, translucent body exhibiting high mechanical strength and toughness. The body evidenced excellent hydrophobic character and moisture pickup after an exposure of three days to a relative humidity of 80% and a temperature of 20° C. was less than 1%, after an exposure of the body for one hour at 110° C.

Illustrative of operable organic chrome complexes are VOLAN and QUILON C, both marketed by E. I. DuPont de Nemours & Co., Inc. Wilmington, Delaware. VOLAN is a chemically reactive Werner complex, methacrylato chromic chloride, wherein methacrylic acid is coordinated with chromium. A reactive, unsaturated organic group is present which can combine with a variety of thermosetting resins such as modified polyester, phenolic, and epoxy resins. QUILON C is a chemically reactive Werner complex wherein a $C_{14}$-$C_{18}$ fatty acid is coordinated with trivalent chromium. The fatty acid group imparts water repellent and release properties. Both compounds are miscible with water.

To obtain flocculation of gel prepared in accordance with U.S. Pat. No. 4,239,519, it is only necessary to bring the gel into contact with the organic chrome complex. Hence, adjustment of the pH of the gel and complex is not required. Nevertheless, to insure complete and homogeneous flocculation, mixing of the gel and complex will be accompanied with stirring and sufficient excess of complex will be included to react with and replace all exchangeable $Li^+$ and/or $Na^+$ ions. Any unexchanged complex and released $Li^+$ and/or $Na^+$ ions can be filtered out.

Table II records chemically analytical data relating to the flocculation of VOLAN and QUILON C of a gel prepared from the following composition, exxpressed in terms of weight percent on the oxide basis:

$SiO_2$: 59.1
MgO: 21.3
$Li_2O$: 8.5
F: 11.1

VOLAN is supplied as a solution consisting, in weight percent, of about 20% VOLAN, 40% isopropanol, 30% water, and 10% acetone. QUILON C is also supplied as a solution consisting of, in weight percent, about 25% QUILON C in isopropanol, water, and acetone. A 7% by weight aqueous solution of KCl was prepared and an aqueous gel containing 4.43 grams of mica/100 ml gel was prepared from the above composition. The VOLAN, QUILON C, and KCl solutions were admixed into 100 ml of gel with stirring at room temperature. Flocculation occurred substantially instantaneously.

TABLE II

| Solution | $Li^+$ Ions Released into Filtrate | **Weight % $Li_2O$ Released From Mica |
|---|---|---|
| 20 ml VOLAN | *773 PPM | 4.7 |
| 10 ml QUILON C | 850 PPM | 4.8 |
| 15 ml KCl | 820 PPM | 4.6 |

*PPM = Parts Per Million
**The % $Li_2O$ calculated from the filtrate analysis is somewhat higher than expected because free $Li^+$ ions are always present in the gel from the hydrolysis of the mica.

Upon drying at 110° C. for 1 hour, the VOLAN exchanged material was a turquoise-blue powder which, when hot pressed for one hour at 300° C. under a pressure of 10,000 psi, cross-linked to form a light weight, smooth-surfaced body demonstrating good mechanical strength and toughness. Chemical analysis of the material indicated the VOLAN content to be about 30% by weight.

Upon drying at 110° C. for 1 hour, the QUILON C exchange product was a green, strongly hydrophobic powder. The powder exhibited no tendency to cohere together or to bond to other resins. Left in water for two weeks, the powder remained floating with no apparent change in non-wetting characteristics. Such features strongly recommend the utility of QUILON C in treating mica-containing articles to render them hydrophobic.

To determine the extent to which the organic compounds will replace $K^+$ ions in potassium-containing micas, the following procedure was undertaken. An aqueous gel was prepared from material having the same composition as reported in Table I. The gel was contacted at room temperature with a 7% by weight aqueous solution of KCl and the mixture stirred for 24 hours to essentially totally replace the exchangeable $Li^+$ ions. After adjusting the pH of the $K^+$ ion exchange floc to about 6.5 via the addition of 25% acetic acid solution, a 2% aqueous solution of Z6020 (pH also adjusted to about 6.5) was admixed therein and the mixture was stirred continuously overnight.

An analysis of the liquid indicated a release of $K^+$ ions thereinto equivalent to about 2% by weight $K_2O$. Inasmuch as the total present in the $K^+$ ion exchanged floc was about 6.5% $K_2O$, it would appear that about one-third of the $K^+$ ions were replaced by the aminosilane Z6020.

Similar tests were conducted utilizing VOLAN and QUILON C. The $K^+$ ion exchanged floc had a solids content of about 5.7%. To 20 ml of that floc were added 5 ml of 2% aqueous solutions of VOLAN and QUILON C wherein the pH thereof was raised to about 6.5 through the addition of LiOH. Table III reports chemical analytical data relating to the results of these tests. In each test, 5 ml of the chrome complex solution were admixed with 20 ml of the floc and stirred continuously overnight. To provide a base line, an analysis of the $K^+$ ion content in the floc liquid is recorded.

TABLE III

| Addition | $K^+$ Ions in Floc Liquid | $K^+$ Ions Released from Mica | Weight % $K_2O$ Released from Mica |
|---|---|---|---|
| None | 138 PPM | — | — |
| VOLAN | 680 PPM | 542 PPM | 1.54 |
| QUILON C | 1164 PPM | 1042 PPM | 2.84 |

As can be observed from Table III, based upon the $K_2O$ level in the original $K^+$ ion exchanged floc (6.5%), VOLAN released about 24% and QUILON C released about 44% of the available $K_2O$. The greater action of QUILON C is believed to be due to the fact that it is monomeric, hence smaller, and therefore more capable of penetrating the floc structure.

To investigate the maximum uptake of organic chrome complex, the following test was conducted. An aqueous gel was prepared in accordance with U.S. Pat. No. 4,329,519 from the composition recited below in terms of weight percent on the oxide basis. The gel was contacted at room temperature with a 7% by weight aqueous solution of KCl and the mixture stirred for 24 hours to insure the virtual total replacement of interlayer $Li^+$ and $Na^+$ ions by $K^+$ ions. A chemical analysis of the resultant floc is also reported below in terms of weight percent on the oxide basis.

| Original Composition | | $K^+$ Ion Exchanged Floc |
|---|---|---|
| $SiO_2$ | 59.6 | 58.8 |
| MgO | 25.6 | 24.9 |
| $Li_2O$ | 1.66 | 1.75 |
| $Na_2O$ | 4.10 | 0.57 |
| F | 9.13 | 8.74 |
| $K_2O$ | — | 5.2 |

A slurry of $K^+$ ion exchanged flock having a solids content of about 1.7% was prepared having a pH of 7.3 and a 2% aqueous solution of VOLAN was prepared, the pH thereof being adjusted from 4.45 to 6.5 through the addition of LiOH. Mixtures of slurry and VOLAN in increasing proportions of VOLAN were reacted for four hours with stirring. The mixtures were thereafter filtered, the filtrate analyzed for K+ ions, and one of the washed residues analyzed for chromium and carbon. Table IV records chemical analytical data of the filtrates and residue plus powder x-ray diffraction data.

TABLE IV

| VOLAN Expressed as % of Mica | K+ Ions | % K$_2$O Released from Mica | % Cr in Residue | % C in Residue | d$_{001}$ Spacing from X-ray diffraction |
| --- | --- | --- | --- | --- | --- |
| 0.5 | 52 | 0.36 | — | — | 11.9 |
| 1.5 | 104 | 0.81 | — | — | 11.4 |
| 2.5 | 144 | 1.22 | — | — | 11.5 |
| 5.5 | 204 | 2.17 | — | — | 13.9 |
| 10.5 | 185 | 2.62 | — | — | 14.4 |
| 100 | 197 | 2.49 | 1.69 | 0.60 | 15.6 |

As is apparent from the above data, about 2.5% VOLAN is adequate to remove the K+ ions in the surface. Higher concentrations begin to penetrate the interlayer of the mica, as is evidenced by the increases in the d$_{001}$ spacings in the x-ray diffraction patterns. The carbon and chromium contents of VOLAN are 10.7% and 31%, respectively. Founded upon those values, the maximum pickup of VOLAN by the mica calculated from carbon and chromium analyses amounts to 5.5% and 5.4%, respectively.

The above sets of examples illustrate that both aminosilanes and organic chrome complexes can replace substantially all of the interlayer Li+ ions in the mica and part of the interlayer K+ ions in potassium-version micas. It is difficult to unequivocally confirm the equivalency of ion uptake exercised by the two types of organic cations because of the undetermined extent of polymerization experience by each. Nevertheless, indirect evidence points to the replaceability of about 40% of the K+ ions in the potassium ion exchanged mica.

The above-described sequence of a K+ ion exchange followed by an exchange with the organic cations is of great practical advantage. Thus, the exchange with K+ ions removes the Li+ and/or Na+ ions from the interlayer of the mica crystals and, thereby, significantly improves the resistance of the material to attack by water. This exchange with K+ ions is relatively inexpensive. Thereafter, the exchange of K+ ions with the organic cations will replace up to about 40% of the K+ ions. This latter exchange will, self-evidently, not demand as great a quantity of organic cations as does the full replacement of the interlayer Li+ and/or Na+ ions. Yet, the exchange with the K+ ions not only bonds the organic cations into the mica crystals, but also enables the organic cations to be available as coupling agents with such resins as epoxy, phenolic, polyester, and melamine. Hence, as little as about 2% by weight of the organic cations may be adequate to replace a sufficient number of K+ ions to provide a substantial presence of a coupling agent. It is self-evident that a much greater amount of organic cations would be required to replace all of the interlayer Li+ and/or Na+ ions in the mica to thereby impart hydrophobic character thereto.

We claim:

1. An organic-inorganic composite mass demonstrating hydrophobic behavior consisting essentially of organic polycation-exchanged lithium and/or sodium water-swelling mica crystals selected from the group of fluorhectorite, hydroxyl hectorite, boron fluorphlogopite, hydroxyl boron phlogopite, and solid solutions among those and between those and other structurally-compatible species selected from the group of talc, fluortalc, polylithionite, fluorpolylithionite, phlogopite, and fluorphlogopite, at least a substantial proportion of said crystals exhibiting a morphology of a continuum of flakes, rectangular-like strips, and interwoven ribbons in parallel or sub-parallel zones or sheaths, wherein said strips and ribbons are about 0.5–10 microns in length, about 500 Å–5000 Å in width, and less than 100 Å in thickness, and said flakes are irregularly shaped with diameters between about 0.5–10 microns and cross sections of less than about 100 Å, and said organic polycation being selected from the group of aminosilanes and organic chrome complexes which are chemically reactive Werner complexes.

2. A composite body according to claim 1 wherein said lithium and/or sodium water-swelling mica consists essentially, expressed in terms of weight percent on the oxide basis, of Li$_2$O: 0–12
Na$_2$O: 0–10
Li$_2$O+Na$_2$O: 0.5–14
MgO: 10–38
B$_2$O$_3$: 0–30
Al$_2$O$_3$: 0–10
SiO$_2$: 35–70
F: 0–15
OH: 0–15
F+OH: 4–15

3. A method for preparing an organic-inorganic composite mass demonstrating hydrophobic behavior consisting essentially of organic polycation-exchanged lithium and/or sodium water-swelling mica crystals selected from the group of fluorhectorite, hydroxyl hectorite, boron fluorphlogopite, hydroxyl boron phlogopite, and solid solutions among those and between those and other structurally-compatible species selected from the group of talc, fluortalc, polylithionite, fluorpolylithionite, phlogopite, and fluorphlogopite, which comprises the steps of:

(a) forming a glass-ceramic body consisting essentially of a lithium and/or sodium water-swelling mica selected from the group of fluorhectorite, hydroxyl hectorite, boron fluorphlogopite, hydroxyl boron phlogopite, and solid solutions among those and between those and other structurally-compatible species selected from the group of talc, fluortalc, polylithionite, fluorpolylithionite, phlogopite, and fluorphlogopite;

(b) contacting said body with a polar liquid for a time sufficient to cause swelling and disintegration thereof accompanied with the formation of a gel, at least a substantial portion of the crystals in said gel exhibiting a morphology of a continuum of flakes, rectangular-like strips, and interwoven ribbons in parallel or sub-parallel zones or sheaths, wherein said strips and ribbons are about 0.5–10 microns in length, about 500 Å–5000 Å in width, and less than 100 Å in thickness, and said flakes are irregularly shaped with diameters between about 0.5–10 microns and cross sections of less than about 100 Å; and (c) contacting said gel with a source of organic polycations selected from the group of aminosilanes and organic chrome complexes which are chemically reactive Werner complexes in an amount and for a time sufficient to cause an ion exchange reaction to occur between said organic polycations and essentially all of the $Li^+$ and/or $Na^+$ ions from the interlayer of said crystals.

4. A method according to claim 3 wherein said lithium and/or sodium water-swelling mica consists essentially, expressed in terms of weight percent on the oxide basis, of $Li_2O$: 0–12
$Na_2O$: 0–10
$Li_2O + Na_2O$: 0.5–14
$MgO$: 10–38
$B_2O_3$: 0–30
$Al_2O_3$: 0–10
$SiO_2$: 35–70
F: 0–15
OH: 0–15
F+OH: 4–15

5. A method according to claim 3 wherein said organic polycation is an aminosilane and the pH of said gel and that of said aminosilane are adjusted to between about 6.5–7.

6. A method according to claim 3 wherein said organic chrome complex is selected from the group of a chemically reactive Werner complex, methacrylato chromic chloride, wherein methacrylic acid is coordinated with chromium, and a chemically reactive Werner complex, wherein a $C_{14}$–$C_{18}$ fatty acid is coordinated with trivalent chromium.

7. A method according to claim 3 wherein said organic-inorganic composite mass is formed into a cross-linked body comprising the steps of:

(a) drying said exchanged gel wherein said organic polycation is selected from the group of an aminosilane and a chemically reactive Werner complex, methacrylato chromic chloride, wherein methacrylic acid is coordinated with chromium;

(b) reducing said dried exchanged gel to a powder;

(c) hot pressing said powder to produce a cross-linked, polycation-mica derivative solid body.

8. A method for preparing an organic-inorgranic composite mass demonstrating hydrophobic behavior consisting essentially of potassium ion and organic polycation-exchanged lithium and/or sodium water-swelling mica crystals selected from the group of fluorhectorite, hydroxy, hectorite, boron fluorphlogopite, hydroxyl boron phlogopite, and solid solutions among those and between those and other structurally-compatible species selected from the group of talc, fluortalc, polylithionite, fluorpolylithionite, phlogopite, and fluorphlogopite, which comprises the steps of:

(a) forming a glass-ceramic body consisting essentially of a lithium and/or sodium water-swelling mica selected from the group of fluorhectorite, hydroxyl hectorite, boron fluorphlogopite, hydroxyl boron phlogopite, and solid solutions among those and between those and other structurally-compatible species selected from the group of talc, fluortalc, polylithionite, fluorpolylithionite, phlogopite, and fluorphlogopite;

(b) contacting said body with a polar liquid for a time sufficient to cause swelling and disintegration thereof accompanied with the formation of a gel, at least a substantial portion of the crystals in said gel exhibiting a morphology of a continuum of flakes, rectangular-like strips, and interwoven ribbons in parallel or sub-parallel zones or sheaths, wherein said strips and ribbons are about 0.5–10 microns in length, about 500 Å–5000 Å in width, and less than 100 Å in thickness, and said flakes are irregularly shaped with diameters between about 0.5–10 microns and cross sections of less than about 100 Å;

(c) contacting said gel with a source of $K^+$ ions in an amount and for a time sufficient to cause the essential total replacement of the $Li^+$ and/or $Na^+$ ions in the interlayer of the mica crystals with $K^+$ ions through an ion exchange reaction therebetween; and (d) contacting said $K^+$ ion exchanged gel with a source of organic polycations selected from the group of aminosilanes and organic chrome complexes which are chemically reactive Werner complexes in an amount and for a time sufficient to cause the replacement of up to about 40% of the $K^+$ ions in the interlayer of the mica crystals with organic polycations through an ion exchange reaction therebetween.

* * * * *